United States Patent [19]

Neier et al.

[11] Patent Number: 4,579,984
[45] Date of Patent: Apr. 1, 1986

[54] PROCESS FOR THE PRODUCTION OF ALCOHOLS

[75] Inventors: Wilhelm Neier; Werner Webers, both of Rheinberg; Michael Dettmer, Glinde; Günther Osterburg, Duisburg, all of Fed. Rep. of Germany

[73] Assignee: Deutsche Texaco Aktiengesellschaft, Hamburg, Fed. Rep. of Germany

[21] Appl. No.: 722,041

[22] Filed: Apr. 11, 1985

[30] Foreign Application Priority Data

May 24, 1984 [DE] Fed. Rep. of Germany ....... 3419392

[51] Int. Cl.$^4$ .............................................. C07C 29/04
[52] U.S. Cl. ...................................... 568/899; 568/895; 568/896; 568/897; 568/899; 568/900; 568/901
[58] Field of Search ...................... 568/899, 895–898, 568/900, 901

[56] References Cited

U.S. PATENT DOCUMENTS

| | | | |
|---|---|---|---|
| 3,994,983 | 11/1976 | Webers et al. | 568/899 |
| 4,087,471 | 5/1978 | Bowman et al. | 568/899 |
| 4,182,920 | 1/1980 | Giles et al. | 568/899 |
| 4,281,206 | 7/1981 | Brandes et al. | 568/899 |
| 4,340,769 | 7/1982 | Brandes et al. | 568/899 |
| 4,351,970 | 9/1982 | Sommer et al. | 568/899 |
| 4,352,945 | 10/1982 | Bezman | 568/899 |
| 4,405,822 | 9/1983 | Bezman | 568/999 |

Primary Examiner—J. E. Evans
Attorney, Agent, or Firm—Robert A. Kulason; James J. O'Loughlin

[57] ABSTRACT

A method is provided for the continuous production of isopropanol and secondary butyl alcohol by catalytically hydrating the corresponding aliphatic olefin in an elongated reaction vessel in which co-product by-product dialkyl ether is separated from the reaction product and recycled to the reaction mixture being introduced therein at a point between the olefin feed inlet and the product outlet about 5 to 30 percent of the distance before the product outlet.

6 Claims, 2 Drawing Figures

PROCESS FOR THE PRODUCTION OF ALCOHOLS

BACKGROUND OF THE INVENTION

This invention relates to a process for the continuous production of isopropyl alcohol and secondary butyl alcohol by the direct hydration of the corresponding olefin with water in the presence of an acidic catalyst at an elevated temperature and pressure. Suitable catalysts for such a reaction include the organic sulfonic acid resins and inorganic porous carrier materials loaded with an acid effective for the process.

The selectivity of such processes is impaired by the simultaneous formation of an aliphatic ether along with the desired alcohol. See "Hydrocarbon Processing", November 1972, pages 113 to 116. It is also known that the formation of the aliphatic ether can be somewhat suppressed in a continuous process by recycling the aliphatic ether into the feedstream for the process. See "Chemical Engineering", Sept. 4, 1972, pages 50 and 51.

DISCLOSURE STATEMENT

U.S. Pat. No. 4,352,945 discloses a process for producing isopropanol in which the by-product diisopropyl ether is subjected to a reversion reaction and the resulting propylene is recycled to the hydration stage of the process.

U.S. Pat. No. 4,340,769 discloses a process for the continuous production of lower aliphatic alcohols in which the reaction is conducted in the presence of a sulfonated styrene-divinyl benzene copolymer catalyst and this disclosure is incorporated herein by reference.

U.S. Pat. No. 4,281,206 discloses the method for preparing lower aliphatic alcohols using a trickle-type fixed-bed catalytic reactor and this disclosure is incorporated herein by reference.

It is an object of the present invention to increase the selectivity of this process for the formation of alcohol without a decrease in efficiency due to the suppression of ether formation or by enlarging the apparatus used for the reaction.

SUMMARY OF THE INVENTION

This invention provides a process for the production of isopropyl alcohol and secondary butyl alcohol by the catalytic direct hydration of the corresponding olefin having from 3 to 4 carbon atoms in an elongated reaction vessel having a feed inlet and a product inlet at opposite ends of the elongated reactor wherein the by-product dialkyl ether produced is recycled and introduced into said reaction mixture at a point spaced about 5 to 30 percent before the outlet of said reactor.

DETAILED DESCRIPTION OF THE INVENTION

In accordance with the process of this invention, an olefin feed, such as propylene or butylene, generally in admixture with water, is introduced into the inlet at one end of an elongated reactor containing an acid hydration catalyst to effect the direct hydration of the olefin to the respective alcohol isopropanol or secondary butanol. The reaction mixture flows essentially over the distance from the feed inlet at one end of the elongated reactor in contact with or over the catalyst toward the outlet at the opposite end of the reactor. Dialkyl ether by-product produced in this reaction is separated from the reaction product and is recycled and introduced into the reaction mixture between said inlet and said outlet at a point about 5 to about 30 percent of the distance between said inlet and said outlet from the exit of the reactor.

According to a preferred embodiment, the ether is charged at a distance about 10 to 20% before the end of the reaction zone.

It has been surprisingly found that the reactor performance can be increased both in a trickle reactor and in a sump reactor, as compared to the conventional process with ether recycling at the olefin feed inlet, if the recycled by-product is not charged to the feed stream, but only shortly before the end of the reaction zone as specified. Although the reaction zone is short (only up to 5–10%, relative to the total length), quantitative splitting of ether is attained, a particularly surprising result. Expressed alternatively, although the recycled ether is injected in that portion of the reaction zone between the olefin feed inlet and the product outlet that falls from 5 to 30% of the distance from the product outlet, the results are surprising.

The figures attached hereto illustrate specific embodiments of the process according to the invention.

Figure 1:
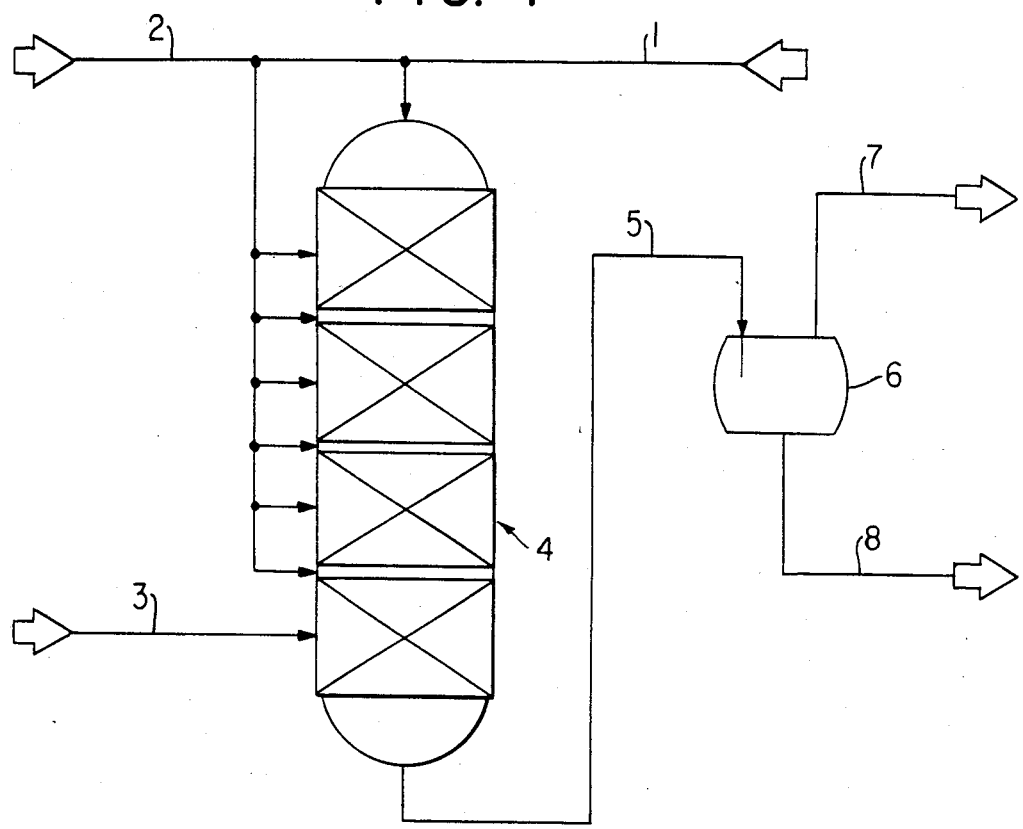
FIG. 1 depicts the scheme of a trickle reactor for the hydration of olefins with controlled ether recycling.

According to FIG. 1, an olefin/alkane mixture is charged through line 1 and process water is charged through line 2 into a tube reactor (4) packed with an acidic catalyst. To better control the reaction heat the water may also be added by sections, as depicted. In an acid-catalyzed multiphase reaction at elevated pressure and temperature the desired alcohol is then formed. The undesired side or secondary reaction forming the ether is suppressed by charging the recycled ether split off from the product. The charging is done through line 3 to the downstream reactor section.

The reaction product is led through line 5 into a separator (6) where it is split up into an organic phase, line 7, and an aqueous phase, line 8. The two phases are worked up by known methods. The separated olefin from the organic phase may be recycled, depending on the desired degree of conversion. The separated ether is recycled through line 3 to the process. The specific reactor efficiency, alcohol formed per catalyst volume and time, is equal to or higher than the efficiency of a corresponding reactor without ether feeding. It is higher than that of a reactor with ether recycling through line 1.

Figure 2:
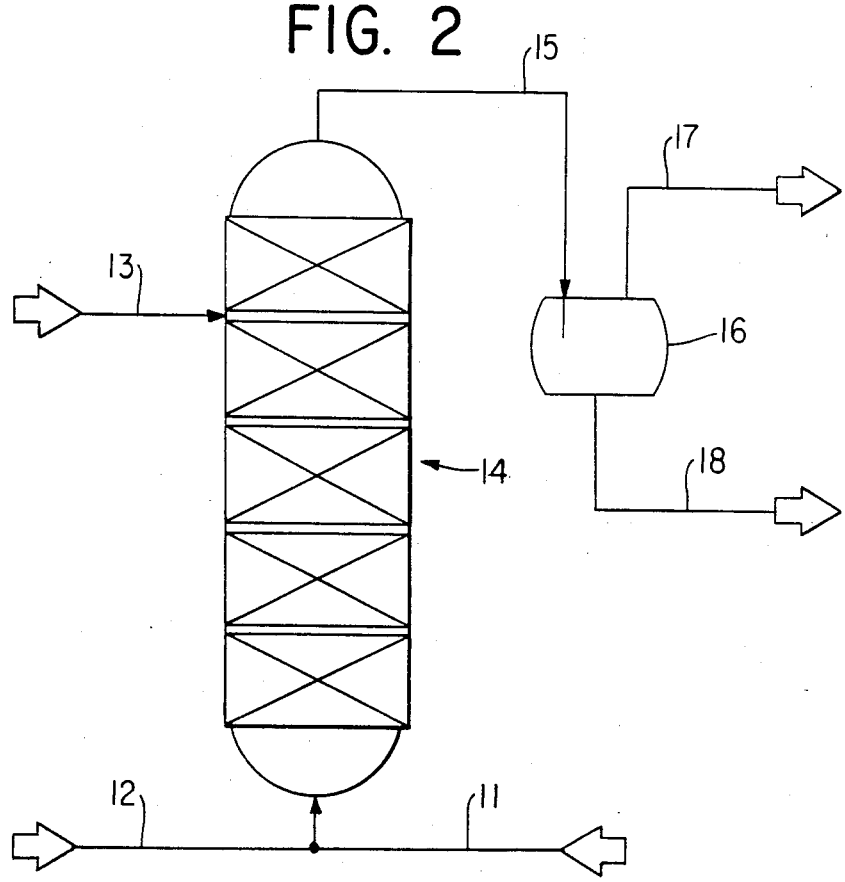
FIG. 2 depicts the scheme of a sump reactor for the hydration of olefins with controlled ether recycling.

FIG. 2 illustrates an example using a sump reactor (14). Olefin and process water are charged to the reactor through lines 11 and 12, respectively. The ether separated from the product stream is recycled through line 13 to the back section of the reactor. In separator 16 the product stream is split up into an organic phase, stream 17, and an aqueous phase, stream 18. Work up is done in the usual way. The separated olefin may be reacted once more if necessary. Reactor efficiency is similar to that obtained in the trickle reactor.

A conventional catalyst for the hydration of olefins is used. Temperature-stable ion exchange resins of the sulfonic acid type are particularly preferred.

The reaction temperatures range between 100° and 200° C. The pressure ranges between 40 and 120 bar. The mole ratio of mole of olefin to mole of water is 0.5:1 to 30:1. Two-phase operation using vaporous olefins and liquid water is preferred.

The amount of ether to be recycled ranges between 5 and 30% wt., relative to the olefin portion.

The following examples illustrate the practice of this invention with reference to the attached figures.

COMPARISON EXAMPLE 1

74.1 kgs/h of a 92% propylene were charged through line 1 and 540 kgs/h of demineralized water were charged through line 2 into the trickle reactor (4) which had a length of 9 meters and a diameter of 280 mm and which was packed with 450 liters of Amberlite 252, a strongly acidic cation exchange resin. Both streams were heated at reaction temperature in preheaters and were charged to the top of trickle reactor 4. To control the temperature, part of the water was branched off before the preheater and was charged to the reactor at different spots. In this test run no ether was charged through line 3 to the reactor.

In separator 6 the product stream 5 was split up into an aqueous phase and an organic phase.

29.4 kgs/h of organic phase with the following average composition were obtained via line 7: 62.5% propane/propylene; 17.0% diisopropyl ether (DIPE); 20.4% isopropyl alcohol (IPA).

583 kgs/h of aqueous IPA containing 11.5% IPA and 0.1% DIPE were obtained via line 8.

The reaction pressure was 100 bar, the mean reaction temperature was 142° C.

In this test run 73.0 kgs/h of IPA and 5.6 kgs/h of DIPE were obtained. The catalyst efficiency was 2.70 moles/l of cat.·h, the ether formation was 7.1% (IPA+-DIPE=100%), and the olefin conversion was approx. 80%.

COMPARISON EXAMPLE 2

The test run described in comparison example 1 was repeated, the difference being that instead of a 92% propylene the same amount of an 80% propylene was used. The other conditions remained unchanged. 54.1 kgs/h of IPA and 7.5 kgs/h of DIPE were obtained.

The catalyst efficiency was 2.00 moles of IPA/l of cat.·h, the ether formation was 12.2% (IPA+-DIPE=100%).

COMPARISON EXAMPLE 3

In accordance with U.S. Pat. No. 2,050,445 the test run described in comparison example 1 was repeated, the difference being that 7.0 kgs/h of DIPE were fed to stream 1. The other reaction conditions remained unchanged. The propylene conversion dropped to 59%. 54.1 kgs/h of IPA and 9.5 kgs/h of DIPE were obtained.

The catalyst efficiency was 2.00 moles of IPA/l of cat.·h, the ether formation was 4.4%.

COMPARISON EXAMPLE 4

The test run described in comparison example 2 was repeated, the difference being that 7.0 kgs/h of DIPE were additionally charged to the feedstream. The other conditions remained unchanged.

43.2 kgs/h of IPA and 10.1 kgs/h of DIPE were obtained.

The catalyst efficiency was 1.6 moles of IPA/l of cat.·h, the ether formation was yet 6.7%.

EXAMPLE 1

The test run described in comparison example 3 was repeated, the difference being that the 7.0 kgs/h of DIPE were charged only one meter before the end of the 9-meter-long catalyst zone. The other conditions remained unchanged.

The propylene conversion was 78% on an average. 76.0 kgs/h of IPA and 7.0 kgs/h of DIPE were obtained.

The catalyst efficiency was 2.81 moles of IPA/l of cat.·h. No ether was formed in the synthesis.

EXAMPLE 2

The test run described in example 1 was repeated, the difference being that the ether feed was increased to 9 kgs/h.

76.9 kgs/h of IPA and 7.1 kgs/h of DIPE were obtained.

The catalyst efficiency was 2.84 moles of IPA/l of cat.·h. Additionally, DIPE was backreacted to IPA.

EXAMPLE 3

The test run described in comparison example 4 was repeated, the difference being that the 7.0 kgs/h of ether were charged one meter before the end of the catalyst zone. The other conditions remained unchanged.

58.5 kgs/h of IPA and 7.6 kgs/h of DIPE were obtained.

The catalyst efficiency was 2.15 moles of IPA/l of cat.·h. The ether formation was 1.0%.

EXAMPLE 4

The test run described in example 3 was repeated, the difference being that the DIPE feed was increased from 7.0 kgs/h to 9.0 kgs/h.

Like in example 3, 58.5 kgs/h of IPA and 7.6 kgs/h of DIPE were obtained. Additionally, diisopropyl ether was backreacted to IPA.

COMPARISON EXAMPLE 5

2,000 g/h of water were fed through line 12, and 527 g/h of a C4-cut containing 98.9% n-butenes and 8,270 g/h of a 90% butene recycle stream were charged through line 11 to sump reactor 14 having a length of 13.5 m and a free cross-sectional area of 5 cm$^2$ and being packed with 6.75 l of Amberlite 252, a strongly acidic cation exchange resin. The pressure in the reactor was 60 bar. The jacket-heated reactor and the preheater (not depicted) were kept at a temperature of 155° C. In the separator (16) the product stream (15) was split up into an aqueous phase and an organic phase.

1,830 g/h of an aqueous solution containing 1.1% SBA were obtained via line 18. The organic phase was split up by continuous distillation. 580 g/h of secondary butyl alcohol (SBA), 17 g/h of diisobutyl ether (DIBE), and 40 g/h of water were separated from the liquefied C4-gas phase. 8,330 g/h of liquefied gas containing 90% n-butene were obtained. Due to the alkane portion in the feed gas part of this gas had to be phased out, the remaining 8,270 g were recycled as mentioned above through line 11 to the reactor.

600 g/h of SBA and 17 g/h of DIBE were obtained. The n-butene conversion was 90%. The reactor efficiency was calculated to be 1.20 moles/l·h, the ether content (SBA+DIBE=100%) was 2.8%.

COMPARISON EXAMPLE 6

The test run described in comparison example 5 was repeated, the difference being that 1,140 g/h of DIBE were added to the C$_4$-gas stream. To maintain the conversion at a constant level, the feed gas stream had to be throttled to 189 g/h.

In this test run 495 g/h of SBA and 900 g/h of DIBE were obtained. Hence, 240 g/h of DIBE were split, the efficiency decreasing at the same time to 0.99 mole/l·h.

EXAMPLE 5

The test run described in comparison example 5 was repeated, the difference being that additionally 690 g/h of DIBE were fed through line 13 at 2.5 m before the end of the reactor. At the same time the amount of C$_4$-feed gas was lowered to 527 g in order to maintain the conversion of butene to SBA at the same level.

20 g/h of SBA were obtained with the aqueous phase from separator 16. Besides 580 g of SBA also 690 g of DIBE were separated from the organic phase so that no ether was formed in the synthesis. Like in comparison example 5, the reactor efficiency was 1.20 moles/l·h.

EXAMPLE 6

The test run described in example 5 was repeated, the difference being that the amount of DIBE fed through line 13 was increased to 1,140 g/h. At the same time the feed gas portion could be lowered to 437 g/h.

The formation of alcohol was the same as in example 5, 990 g/h of DIBE were separated.

Under these conditions of this test, 150 g/h of DIBE were hydrated to alcohol, the efficiency remaining unchanged.

We claim:

1. In a process for the production of an aliphatic alcohol by the catalytic direct hydration of an olefin having from 3 to 4 carbon atoms in an elongated reactor having an olefin feed inlet and a product outlet disposed at opposite ends of said reactor and in which the olefin-water reaction mixture flows a distance from said inlet through an elongated reaction zone to said outlet in which process both said aliphatic alcohol and by-product dialkyl ether are formed, the improvement which comprises:

introducing recycled dialkyl ether into said reaction mixture between said inlet and said outlet at a point about 5 to 30 percent of said distance from said outlet of said reactor.

2. A process according to claim 1 in which said dialkyl ether is introduced into said reactor at a point spaced about 10 to 20 percent before the outlet in said reactor.

3. A process according to claim 1 in which said reactor is a downward flow trickle-type reactor.

4. A process according to claim 1 in which said reactor is an upward flow sump type reactor.

5. A process according to claim 1 in which said olefin is propylene and said alcohol is isopropanol.

6. A process according to claim 1 in which said olefin is an n-butene and said alcohol is sec-butanol.

* * * * *